United States Patent
Hortobágyi et al.

(10) Patent No.: US 10,981,884 B2
(45) Date of Patent: Apr. 20, 2021

(54) PROCESS FOR THE PREPARATION OF EPOPROSTENOL SODIUM OF ENHANCED STABILITY

(71) Applicant: CHINOIN GYÓGYSZER ÉS VEGYÉSZETI TERMÉKEK GYÁRA ZRT., Budapest (HU)

(72) Inventors: Irén Hortobágyi, Budapest (HU); István Lászlófi, Budapest (HU); Zsuzsanna Kardos, Budapest (HU); József Molnár, Budapest (HU); László Takács, Budapest (HU); Róbertné Tormási, Budapest (HU)

(73) Assignee: CHINOIN PHARMACEUTICAL AND CHEMICAL WORKS PRIVATE COMPANY LTD., Budapest (HU)

( * ) Notice: Subject to any disclaimer, the term of this patent is extended or adjusted under 35 U.S.C. 154(b) by 158 days.

(21) Appl. No.: 16/087,388

(22) PCT Filed: Mar. 21, 2017

(86) PCT No.: PCT/EP2017/056690
§ 371 (c)(1),
(2) Date: Sep. 21, 2018

(87) PCT Pub. No.: WO2017/162668
PCT Pub. Date: Sep. 28, 2017

(65) Prior Publication Data
US 2020/0123124 A1 Apr. 23, 2020

(30) Foreign Application Priority Data
Mar. 23, 2016 (HU) .................. P1600211

(51) Int. Cl.
*C07D 307/937* (2006.01)
*A61K 9/19* (2006.01)

(52) U.S. Cl.
CPC ............ *C07D 307/937* (2013.01); *A61K 9/19* (2013.01)

(58) Field of Classification Search
CPC .................................... C07D 307/937
USPC ........................................ 549/465
See application file for complete search history.

(56) References Cited

FOREIGN PATENT DOCUMENTS

EP          0005768 A1    12/1979
WO    WO 2007/092343 A2    8/2007

OTHER PUBLICATIONS

Hungarian Search Report for Hungarian Application No. P1600211, dated Oct. 13, 2016, with English translation.
International Search Report and Written Opinion of the International Searching Authority (Forms PCT/ISA/210 and PCT/ISA/237) for International Application No. PCT/EP2017/056690, dated May 17, 2017.
Johnson et al., "Synthesis and Characterization of Prostacyclin, 6-Ketoprostaglandin $F_1\alpha$, Prostaglandin $I_1$, and Prostaglandin $I_3$," Journal of the American Chemical Society, Nov. 22, 1978, pp. 7690-7705.
Tömösközi et al., "A Simple Synthesis of $PGI_2^1$," Tetrahedron Letters, No. 30, 1977, pp. 2627-2628.

*Primary Examiner* — Patricia L Morris
(74) *Attorney, Agent, or Firm* — Birch, Stewart, Kolasch & Birch, LLP

(57) ABSTRACT

The invention provides a stable epoprostenol sodium and a process for the preparation this pharmaceutically active ingredient.

9 Claims, No Drawings

PROCESS FOR THE PREPARATION OF EPOPROSTENOL SODIUM OF ENHANCED STABILITY

The subject of our invention is stable epoprostenol sodium which can be stored in deep freezer (−20±5° C.) for at least 3 years, and process for its preparation.

Epoprostenol sodium of formula I is the synthetically produced sodium salt of the natural prostacyclin of formula IV. The names prostacyclin Na and epoprostenol Na are equal.

The main therapeutic field of epoprostenol Na is treatment of pulmonary hypertension (PAH) (European Heart J., 2004, 25, 2243-2278).

Since its isolation in 1976 (Nature, 1976, 263, 663-665) it is known that prostacyclin is the metabolite of arachidonic acid and it possesses strong vasodilatory and platelet aggregation inhibitory effect.

It also became clear very soon that the molecule is chemically highly instable, in neutral or acidic aqueous solutions it transforms into the biologically inactive 6-oxo-$PGF_{1alpha}$ of formula V (Schema 1.)

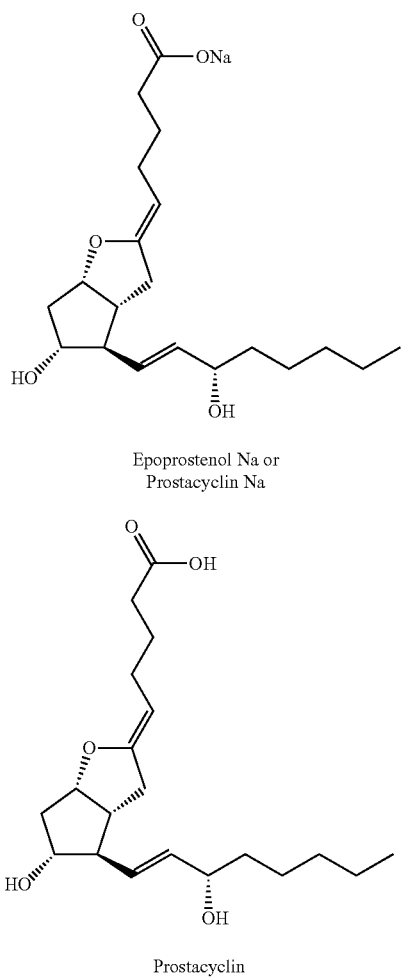

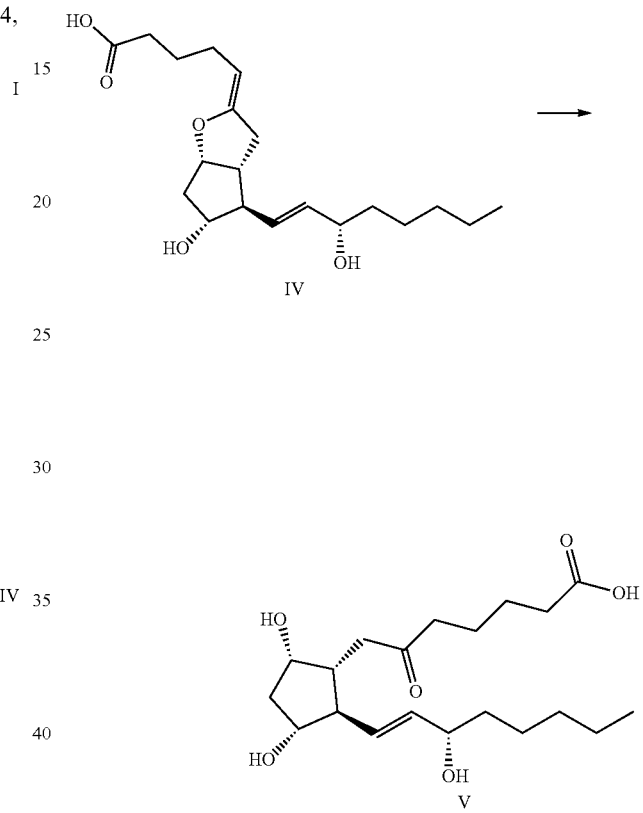

Schema 1.

The reason for its extremely fast degradation (its half-life in aqueous solution at physiological pH is 3-4 minutes) is that beside the enol-ether structure, the chain-end carboxylic group accelerates the decomposition both in its protonated and ionized forms (J. C. S. Chem. Comm., 1979, 129-130). The first, and also structure-proving synthesis was performed by Corey and his group starting from $THP_2$-$PGF_{2alpha}$ (J. A. Chem. Soc., 1977, 99, 2006-2008).

The process is shown in Schema 2.

Schema 2.

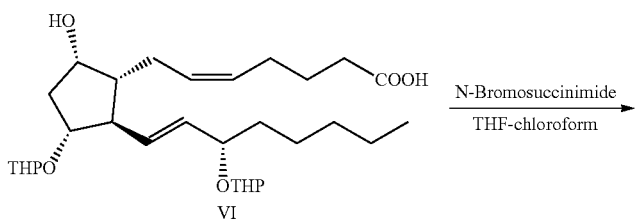

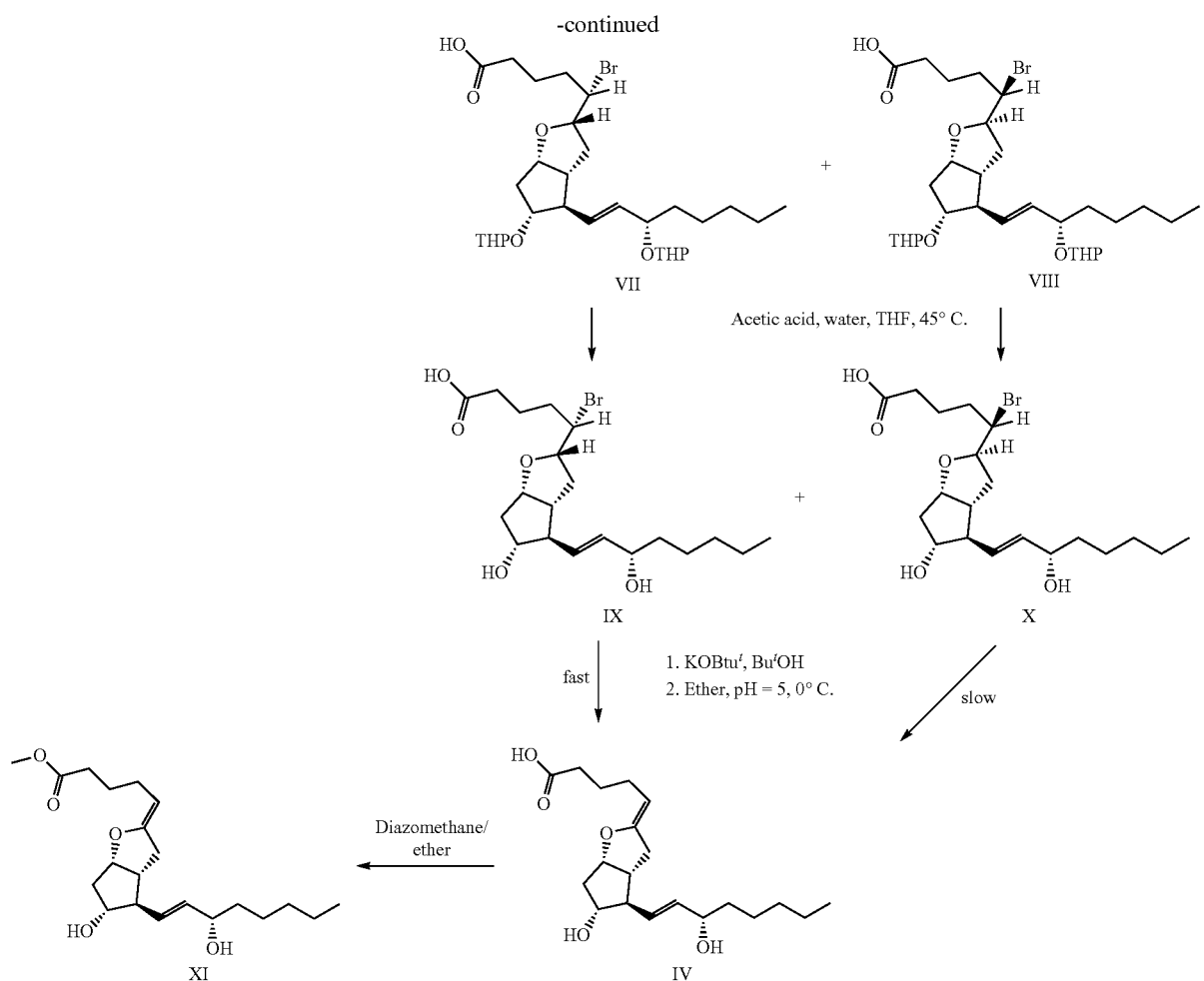

In the process THP$_2$—PGF$_{2alpha}$ of formula VI was reacted with N-bromosuccinimide to obtain the bromo ether diastereomers of formulae VII and VIII. After removal of the THP-group (tetrahydropyranyl group) the diastereomers of formulae IX and X were separated by chromatography. The isomer of formula IX, which contains the bromo substituent in the sterically less hindered (exo) position, on treatment with potassium tertiary-butylate in tert-butanol converted under hydrogen bromide elimination into the enol-ether of formula IV within 1.5 hours. The enol-ether was separated from the mild acidic aqueous solution by fast etheral extraction and was then transformed with diazomethane into the methyl ester of formula XI.

The isomer of formula X, which contains the bromo substituent in the sterically hindered (endo) position, reacted under the above conditions only to a small extent.

The methyl ester of formula XI in acidic medium is transformed into the 6-oxo-PGF$_{1alpha}$ methyl ester of formula XII, this transformation is, however, more slowly than the hydrolysis of prostacyclin (Schema 3.).

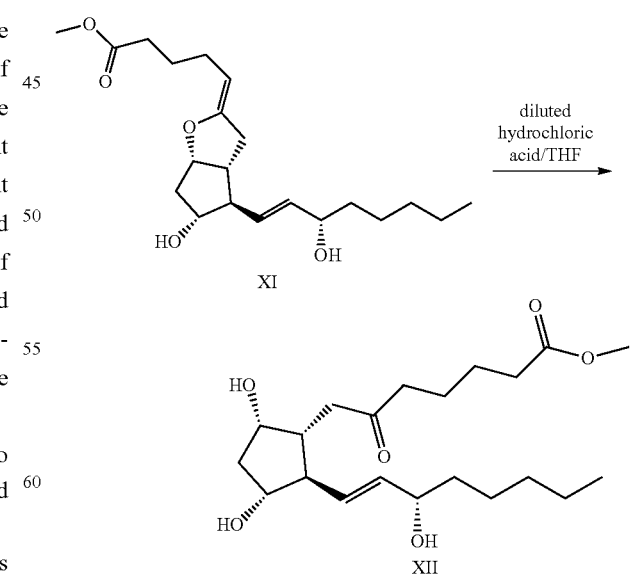

Schema 3.

The first synthesis was followed almost simultaneously by numerous other preparations. Key steps of the syntheses are halocyclisation of the PGF$_{2alpha}$ or its derivative followed by hydrogen halogenide elimination on the effect of base. Due to the chemical instability of the free acid, the product was always isolated and stored in the form of its salt.

Tömösközi and his co-workers were the first to prove (Tetrahedron Letters, 1977, 30, 2627-2628) that
- the bromo- and the iodo-cyclisation reaction can also be realized from the unprotected PGF$_{2alpha}$ and its methyl ester,
- both halo ether diastereomers transform into the cis-vinyl ether derivative (prostacyclin) on the effect of bases,
- the hydrogen halogenide elimination is faster in the case of the iodo-derivative, hydrogen iodide eliminates from the iodo-derivative even on the effect of potassium carbonate.

In the halocyclisation reaction
- as iodine source, KIO$_3$+KI in acetic acid-water mixture as solvent, or I$_2$ in pyridine, or ICl in acetonitrile were applied,
- as bromine source N-bromosuccinimide in dichloromethane, or dibromodimethylhydantoine in dichloromethane and acetonitrile, or N-bromocamphorimide in dichloromethane were applied.

The hydrogen halogenide elimination was effected with potassium ethylate or potassium tertiary-butylate bases in the appropriate alcohol. In the case of iodo substituent the elimination took place even on the effect of potassium carbonate.

Johnson and his co-workers (J. Am. Chem. Soc., 1977, 99, 4182-4184) were the first to prepare lyophilized prostacyclin sodium salt by hydrolysis of the methyl ester of formula XI with equivalent amount of sodium hydroxide in methanol:water=1:1 mixture, followed by lyophilisation of the obtained reaction mixture containing the epoprostenol sodium salt. The lyophilisate, white powder, remained stable for at least two months at −30° C.

The methyl ester was prepared from the PGF$_{2alpha}$ methyl ester, applying as iodine source KI-I$_2$ reagent in water or in dichloromethane solvent, in the presence of sodium carbonate.

Reaction conditions of the hydrogen iodide elimination:
- with silver carbonate in tetrahydrofuran in the presence of traces of perchloric acid
- with 1,5-diazabicyclo[4.3.0]non-5-ene (DBN) base, in benzene
- with potassium superoxide (KO$_2$) in dimethylformamide in the presence of 18-cown ether.

Whittaker (Tetrahedron Letters, 1977, 32, 2805-2808) prepared the iodo ether diastereomers of formula XIV from PGF$_{2alpha}$ methyl ester. The iodine source, aqueous KI-I$_2$ reagent, was added dropwise to the ether solution of PGF$_{2alpha}$ methyl ester, the ether was previously saturated with aqueous sodium hydrogen carbonate solution. Better result was reached when the iodine was dissolved in ether or dichloromethane.

The iodo ether diastereomers were treated in methanol with 10 equ. sodium methylate. After the hydrogen iodide elimination the ester group was hydrolyzed with 1N sodium hydroxide solution. From the concentrated aqueous reaction mixture the epoprostenol sodium salt crystallized in the form of fine needles.

The salt was filtered off, washed with 1N sodium hydroxide and dried on the air, while the surface of the crystals in about 3.5% became covered with sodium carbonate, which protected the enol-ether structure product. The sodium salt was stored in sealed tube.

The process is demonstrated in Schema 4.

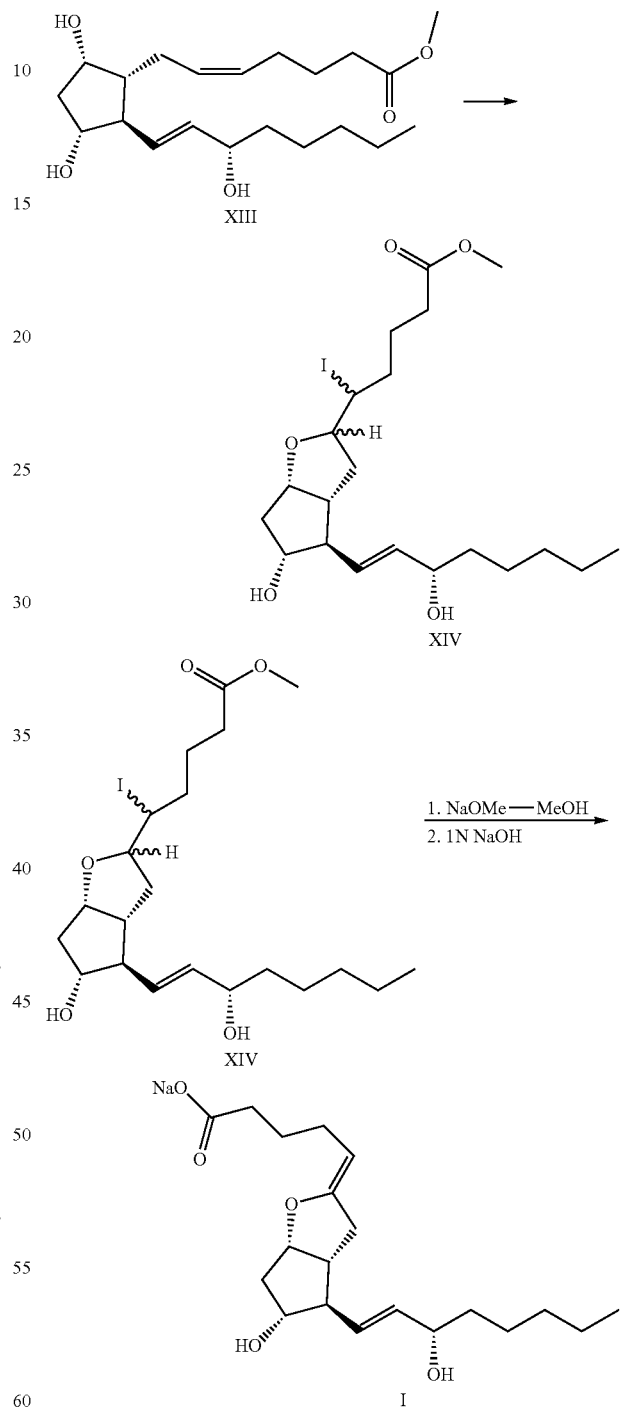

Schema 4.

Nicolau and his co-workers (J. C. S. Chem. Comm., 1977, 630-631) reacted the PGF$_{2alpha}$ methyl ester of formula XIII with iodine in dichloromethane, in the presence of potassium carbonate. Hydrogen iodide elimination from the diastereomers of formula XIV was effected in toluene at 110° C. with 1,5-diazabicyclo[5.4.0]undec-5-ene (DBU) base or, more preferably in methanol, in the presence of sodium methylate.

If the iodo ether diastereomers of formula XIV were treated with sodium methylate in methanol containing 5% of water, beside the hydrogen iodide elimination, hydrolysis of the ester group also took place (Schema 5.), and the resulting epoprostenol sodium salt remained stable in the solution. The prostacyclin Na stock solution was used after further dilution for biological studies.

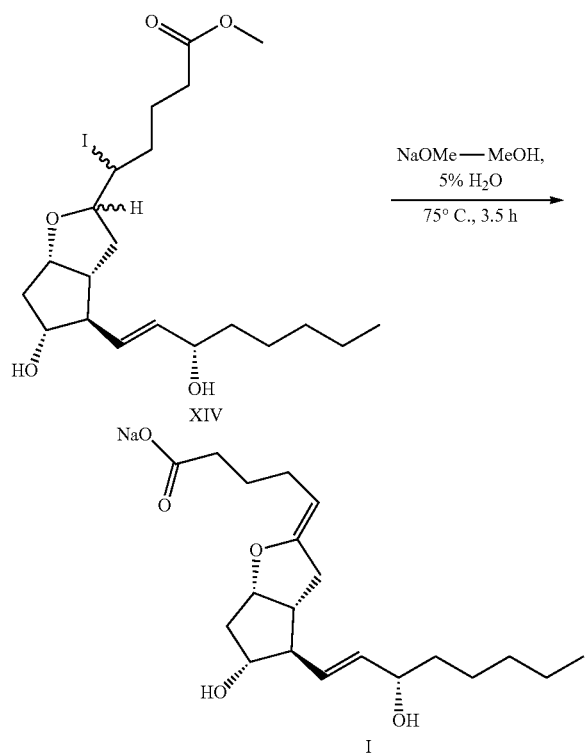

Johnson and his co-workers, in their publication in 1978 (J. Am. Chem. Soc., 1978, 100, 7690-7705) described the preparation of prostacyclin Na and its isomeric impurities. The most detailed description of the synthesis was published in 1982 (Methods in Enzymology, 1982, 86, 459-446). It relates to the synthesis of prostacyclin Na.

The starting material is the $PGF_{2alpha}$ methyl ester of formula XIII, it was dissolved in dichloromethane, to the solution saturated sodium hydrogen carbonate solution was added and to the resulting suspension, under intensive agitation at 0° C., the solution of iodine in dichloromethane was added. At the end of the reaction the phases were separated, the aqueous phase was extracted with dichloromethane, the united organic phase was washed first with sodium sulphite solution then with saturated salt solution, then dried over sodium sulphate, filtered and evaporated in vacuum. The product is the 10:1 ratio mixture of the iodo-ether diastereomers of formula XIV.

The iodo-ether diastereomers were dissolved in water-free diethyl ether and using DBN or DBU base the hydrogen iodide elimination was effected. At the end of the reaction ether was distilled off in vacuum, the product was extracted with ether:hexane:triethylamine=1:1:0.02 mixture and purified by chromatography. The evaporated main fraction, the prostacyclin methyl ester could directly be carried into the next step, or crystallized from ether:hexane:0.01% triethylamine solvent mixture. Yield: 60%, mp: 56-58° C.

The obtained prostacyclin methyl ester was dissolved in carbon dioxide-free methanol, equimolar amount of 1N sodium hydroxide solution was added and the mixture was reacted in an inert atmosphere at 40° C. for 3 hours. At the end of the hydrolysis, methanol was added and the reaction mixture was concentrated. The residue was dissolved in water and crystallized with acetonitrile. The resulting fluffy prostacyclin Na crystals were kept in vacuum exsiccator.

Yield: 82%.

According to the method described in patent specification GB 1583961 the $PGF_{2alpha}$ methyl ester of formula XIII was dissolved in diethyl ether, to this solution first aqueous sodium hydrogen carbonate solution and then, dropwise, aqueous potassium iodide-iodine solution were added. The mixture was agitated overnight at room temperature, then ether was added, the mixture was washed with aqueous sodium thiosulphate, then with water, dried and evaporated. The residue (iodo-ether diastereomers of formula XIV) was reacted with sodium methylate in methanol in an inert atmosphere, methanol was then removed in vacuum. The residue (prostacyclin methyl ester of formula XI, amorphous solid material) was washed with benzene and treated with 1N sodium hydroxide, while it transformed into colorless needles of prostacyclin Na.

The authors simplified the method by leaving out the evaporation of the iodo-ether diastereomers, instead, they added aqueous 1N sodium hydroxide solution into the sodium methylate in methanol solution. At the end of the hydrolysis methanol was removed and from the remaining aqueous solution the prostacyclin sodium crystallized in the form of fine needles.

From the cited literature it turns out that as regards chemistry, the preparation of epoprostenol Na (prostacyclin Na) starting from $PGF_{2alpha}$ is solved.

The problem remained, however, how to keep the drug substance and drug product, because of the chemical instability of epoprostenol.

According to the above described methods
the lyophilized sodium salt was stored at −30° C. for two months, or
it was isolated by crystallization and the surface of the crystals was covered and stabilized with sodium carbonate, then it was stored in closed tube, protected from the air, or
from the sodium salt a stock solution was prepared and this was stored in the form of solution, or
the crystalline salt was stored in vacuum exsiccator.

To improve the stability of epoprostenol Na drug substance and finished product is an important object, because a sterile pharmaceutical composition is expected to keep its drug substance content at room temperature for 12 hour or, if this cannot be reached, it must be stable at 4° C. for 12 hours.

Stability of the pharmaceutical product FLOLAN® (GlaxoSmithKline, 1995) which contains epoprostenol Na drug substance "injection sterile sodium salt formulated for intravenous usage" is ensured by setting its pH to a value of approx. 10.5.

FLOLAN® is a white or almost white powder. Each ampoule contains an amount of sodium salt equivalent to 0.5 mg or 1.5 mg of epoprostenol, 3.76 mg of glycine, 2.93 mg of sodium chloride, 50 mg of mannitol, and in addition sodium hydroxide for pH adjustment.

For intravenous application FLOLAN® has to be dissolved in a specific dissolution mixture (50 ml colorless buffer solution consisting of 94 mg of glycine, 73.3 mg of sodium chloride, water suitable for injection preparation and sodium hydroxide).

The pH of FLOLAN® solution is 10.2-10.8. If the prepared FLOLAN® solution is not used immediately, it may be stored, while protected from light, at 2-8° C. for maximum 2 days, and it may not be deep frozen again.

At a lower pH value the stability of FLOLAN® solution decreases significantly.

The novelty of the method described in patent application WO2007/092343 is that in the presence of at least one alkalizing agent at a high pH value, at pH>11, the stability of the epoprostenol solution increases significantly, compared to that of FLOLAN®.

In the specification the preparation of a bulk solution is described which contains epoprostenol or epoprostenol salt, one alkalizing agent and excipients, and the pH of the solution is set to pH>11, preferably to 12.5-13.5, preferably to 13. The thus obtained solution is then lyophilized, the parameters of the lyophilisation process are also given in the specification.

Before intravenous application, the lyophilisate is dissolved, the pH of the obtained (diluted) solution is also >11.

This solution of high pH may be used for therapeutic aims equally to FLOLAN® solution. Due to its higher pH the solution at room temperature keeps 90% of its active ingredient content for 14-48 hours.

Owing to this enhanced stability, no specific solvent for the dissolution is required, any of the commercially available solutions for intravenous application may be used.

The solution is more resistant against microorganisms.

According to the patent specification
- the ratio of the amounts of epoprostenol or epoprostenol salt and the alkalizing agent may be 1:25-1:200
- The alkalizing agent ensures the alkaline medium but does not contain basic hydroxyl group, it may be arginine, lysine, meglumine, N-methyl-glucosamine, pKa>9.0 amino acid, sodium triphosphate, sodium carbonate, EDTA tetra-sodium salt.
- the amount of the excipient is 1-10%
- The excipient may be hydroxy ethyl starch, sorbite, lactose, dextran, maltose, mannose, ribose, sucrose, mannite, trehalose, cyclodextrine, glycine and polyvinylpyrrolidone.
- the epoprostenol salt is preferably sodium salt
- the pH of the solution is set with inorganic or organic bases
- The inorganic base is sodium hydroxide, potassium hydroxide, magnesium hydroxide or ammonium hydroxide.
- The organic base is aromatic amine or aromatic alcohol.
- the solution is lyophilized in sterile vial.

The composition of most favoured formulation contains 0.5 mg of epoprostenol (or equivalent amount of salt), 50 mg of arginine and 50 mg of mannite, the pH of the solution is then set to 13 and lyophilized.

The lyophilisate is dissolved in 50 ml of solvent, the pH of the obtained solution is >11 (according to the examples: 11.58-11.6).

The thus prepared epoprostenol solution is more stable than the FLOLAN® solution after setting to similar pH (pH=13).

According to our invention the epoprostenol sodium is prepared in the shortest way, in two reaction steps starting from the unprotected PGF$_{2alpha}$ (formula III) (Schema 6.).

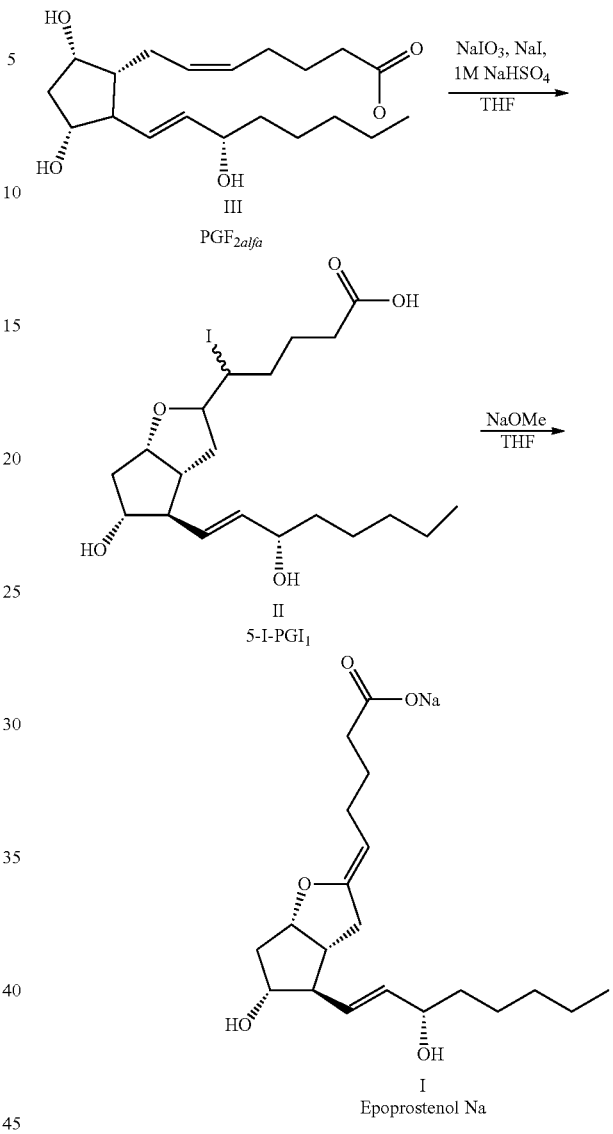

Advantage of our method, as compared to earlier methods, is that it does not contain halogenated or other environmentally harmful solvents.

Both reaction steps are performed in tetrahydrofuran, therefore, after the first step it is enough to concentrate the reaction mixture, lengthy, time-consuming full evaporation which may harm the sensitive iodo derivative of formula II is unnecessary.

The iodine source for the iodo-cyclisation is the reaction of sodium iodide-sodium iodate taking place in acidic medium.

During the reaction the sodium iodide which is formed beside the product continuously reacts with the sodium iodate, and the resulting iodine is used in the iodo-cyclisation.

If we choose a reaction mixture of PGF$_{2alpha}$:NaI:NaIO$_3$=3:2:1 ratio, then the utilization of the iodine is nearly 100%, it means that our method does not pollute the environment.

Hydrogen iodide elimination is effected with sodium methylate reagent. At the end of the reaction tetrahydrofuran is distilled off in vacuum, to the residue sodium hydroxide solution is added and the epoprostenol Na salt is crystallized. The precipitated sodium salt is dissolved in water and lyophilized.

We investigated the effect of the sodium hydroxide amount used for the salt formation on the stability of the acid-sensitive epoprostenol Na.

For this purpose the excess alkali which may be present in the epoprostenol Na salt was removed with strongly acidic cation exchange DOWEX resin, to the aqueous solution of the salt not containing excess alkali, different amounts of sodium hydroxide were added and the obtained solutions were lyophilized.

From the 1% aqueous lyophilisate solutions we measured the pH and started accelerated stability studies at room temperature, in closed glass vessels.

The change of the active ingredient content of the stability samples was followed by HPLC after 0, 24, 48 and 144 hours.

From the measured active ingredient contents decomposition rates of epoprostenol Na have been calculated (Table 1.).

TABLE 1

1. Decomposition rate of Epoprostenol Na

| NaOH mass % (added) | pH (1% aqueous solution) | PGI$_2$Na decomposition (%/month) |
|---|---|---|
| 0.25 | 9.98 | 34.9 |
| 0.25 | 10.14 | 34.6 |
| 2.5 | 11.64 | 10.6 |
| 2.5 | 11.64 | 10.9 |
| 3.0 | 11.70 | 8.8 |
| 4.0 | 11.78 | 4.5 |
| 5.0 | 11.86 | 1.7 |
| 5.5 | 11.90 | 1.3 |
| 6.0 | 11.92 | 1.7 |
| 7.5 | 12.00 | 3.1 |
| 12.5 | 12.15 | 3.5 |

To our surprise, we found that on the effect of the added sodium hydroxide excess the stability of the epoprostenol Na significantly increases until approx. 5.5 mass %, then it starts to decrease to a small extent.

To reach this enhanced stability the presence of amino acids or other buffer-effect excipients were not needed.

Based on these unexpected experimental results we modified our new technology, we dissolved the funnel-wet, crystalline epoprostenol sodium salt in water, to the aqueous solution we added 2M NaOH solution in such an amount that the product, after lyophilisation contains 4 mass % excess of sodium hydroxide.

The stability of the epoprostenol Na prepared by this new method is excellent, it can be stored in deep-freezer (−20±5° C.) for at least 3 years. The amount of the 6-oxo-PGF$_{1alpha}$ impurity, characteristic for the decomposition of the product, does not show any change during the storage time (Table 2.).

TABLE 2

Change of the 6-oxo-PGF$_{1alpha}$ content during storage in deep-freezer (−20 ± 5° C.)

| | Month | | | | | | | | |
|---|---|---|---|---|---|---|---|---|---|
| | 0 | 1 | 3 | 6 | 9 | 12 | 18 | 24 | 36 |
| HPLC [mass %] | 0.2 | 0.2 | 0.2 | 0.2 | 0.2 | 0.2 | 0.2 | 0.2 | 0.2 |

The epoprostenol Na prepared by the new method may be stored in refrigerator (5±3° C.) for at least 6 months (Table 3.).

TABLE 3

Change of the 6-oxo-PGF$_{1alpha}$ content during storage in refrigerator (5 ± 3° C.)

| | Month | | | |
|---|---|---|---|---|
| | 0 | 1 | 3 | 6 |
| HPLC [mass %] | 0.2 | 0.3 | 0.4 | 0.2 |

According to our new method, PGF$_{2alpha}$ is dissolved in tetrahydrofuran. The iodine source for the iodo-cyclisation is the sodium iodide-sodium iodate reaction proceeding in acidic medium. At the end of the cyclisation reaction saturated sodium chloride solution is added to the reaction mixture and the product is extracted with tetrahydrofuran-hexane mixture. Excess iodine is removed with sodium metabisulfite solution. The product solution is washed, dried, concentrated to a determined weight and without further purification carried into the next—hydrogen iodide elimination—step.

Hydrogen iodide elimination is carried out in tetrahydrofuran solution using sodium methylate base. At the end of the reaction 2M sodium hydroxide solution is added to the reaction mixture, tetrahydrofuran is removed by distillation and the epoprostenol Na product is crystallized. The crystals are filtered off, washed, and to the product 2M NaOH solution is added in such an amount that the sodium salt after lyophilisation contains 4 mass % excess of sodium hydroxide. The solution is then lyophilized.

The lyophilisate is a white, or almost white powder, it can be stored in deep freezer (−20±5° C.) for at least 3 years, in refrigerator (5±3° C.) for at least 6 months.

In agreement with the above, the subject of our invention is stable epoprostenol sodium which can be stored in deep freezer (−20±5° C.) for at least 3 years, characterized by that the epoprostenol sodium and an inorganic base or a basic-hydrolyzing inorganic salt in 3-7.5 mass % amount, related to the epoprostenol sodium, are stored in lyophilized form.

A further subject of the invention is process for the preparation of stable epoprostenol sodium which can be stored in deep freezer (−20±5° C.) for at least 3 years, characterized by that the aqueous solution of the epoprostenol sodium salt is lyophilized in the presence of an inorganic base or a basic-hydrolyzing inorganic salt ensuring the pH>11 medium.

As inorganic base or basic-hydrolyzing inorganic salt ensuring the pH>11 medium, a sodium cation-containing base or salt is applied.

The inorganic base containing sodium cation may be sodium hydroxide or sodium carbonate, preferably sodium hydroxide, the basic-hydrolyzing inorganic salt may be trisodium phosphate.

According to the invention the epoprostenol sodium lyophilisate contains the inorganic base or the basic-hydrolyzing inorganic salt in a 3-7.5 mass % amount, related to the sodium salt.

The process includes that the aqueous solution of the epoprostenol sodium salt is lyophilized in the presence of such an amount of added sodium hydroxide solution, that the lyophilisate contains 3-7.5 mass %, preferably 4-6 mass % of sodium hydroxide excess. We have found that the preferred 4-5-6% NaOH excesses are equally good in the storage praxis.

Another subject of the invention is process for the preparation of stable epoprostenol sodium by iodo-cyclisation and hydrogen iodide elimination, in a way that a.) as starting material, unprotected $PGF_{2a}$ is used,
b.) as iodine source, sodium iodide-sodium iodate mixture is applied,
c.) the cyclisation and the hydrogen iodide elimination are carried out in the same solvent,
d.) the aqueous solution of the epoprostenol sodium salt is lyophilized in the presence of an inorganic base or basic-hydrolyzing inorganic salt ensuring a pH>11 medium.

According to a preferred embodiment of the invention a reaction mixture of $PGF_2$:sodium iodide:sodium iodate=3:2:1 ratio is applied.

As solvent, tetrahydrofuran is used.

Further details of the invention are demonstrated in the examples, without limiting the invention to the examples.

EXAMPLES

5ξ-iodo-9-desoxy-6ξ,9α-epoxyprostaglandin F1α ($5$-I-$PGI_1$)

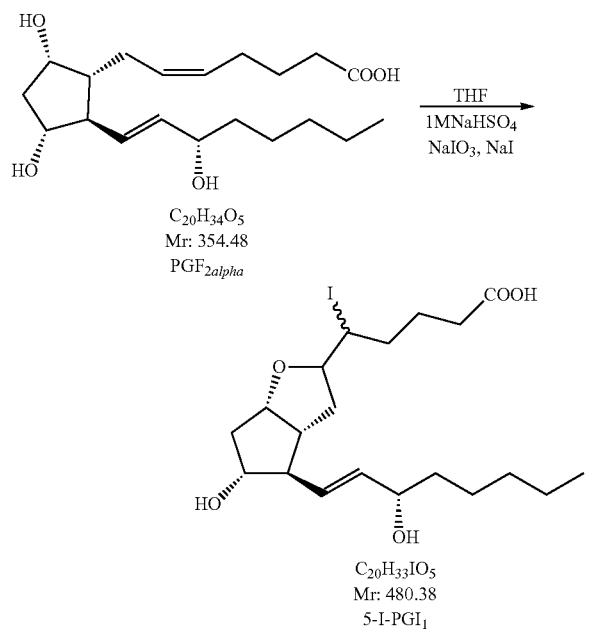

1M sodium hydrogen sulfate solution is prepared from 3 l of water, 87.7 ml of conc. sulfuric acid and 247 g of sodium sulfate. To the solution are added 1.2 l of water, then under stirring the solution of 95.1 g of sodium iodate in 1.2 l of water, the solution of 473.4 g of prostaglandin $F_{2alpha}$ in 1.5 l of tetrahydrofuran, and finally the solution of 148.1 g of sodium iodide in 0.44 l of water. At the end of the reaction saturated sodium chloride solution and tetrahydrofuran:hexane=1:1 mixture are poured onto the reaction mixture. The phases are separated, the aqueous phase is extracted with tetrahydrofuran:hexane=1:1 mixture. The united organic phase is washed with 5% sodium metabisulfite solution, then with diluted and saturated salt solutions, dried over sodium sulfate and concentrated to approx. 1 kg.

The 5-I-$PGI_1$ intermediate is carried into the next reaction step without further purification.

(5Z,9α,11α,13E,15S)-6,9-Epoxy-11,15-dihydroxyprosta-5,13-dien-1-acid sodium salt ($PGI_2$-Na)

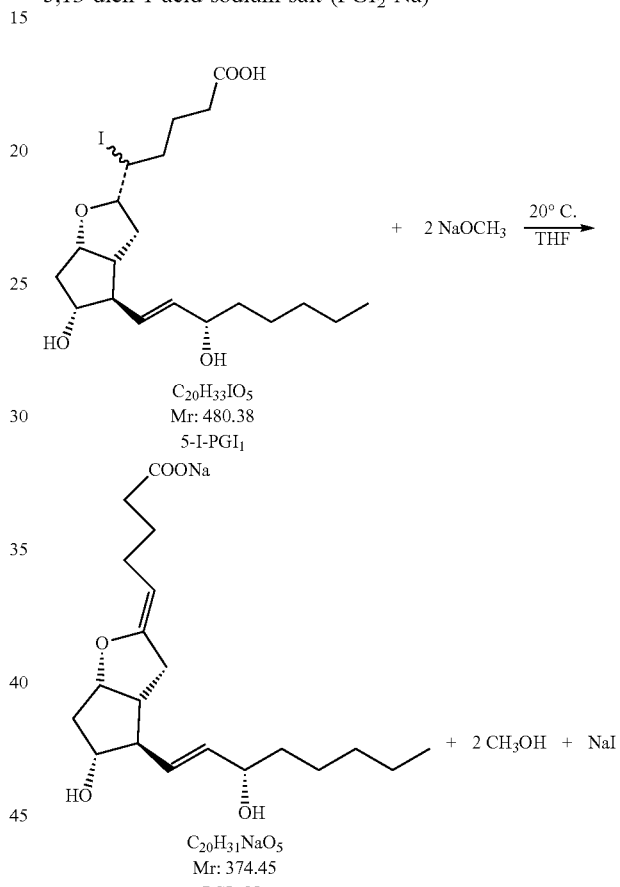

To the 5-I-$PGI_1$ intermediate (concentrated to approx. 1 kg) obtained in the previous step, 12.4 l of water-free tetrahydrofuran and 721 g of sodium methylate are added and the mixture is agitated at room temperature. At the end of the reaction 2 M sodium hydroxide solution is added to the reaction mixture and tetrahydrofuran is distilled off in vacuum. The mixture is agitated at room temperature until a great amount of crystals precipitate, then it is cooled to 0° C. to complete the crystal precipitation. The crystals are filtered off, washed with 2M, and then with 1M sodium hydroxide solutions. The crystals are then dissolved in such an amount of 2M sodium hydroxide solution that the product contains 4 mass % excess of sodium hydroxide. The solution is lyophilized.

Yield: 250 g (50%) as calculated for $PGF_{2a}$, the product is a white powder.

The invention claimed is:

1. Stable epoprostenol sodium drug substance which can be stored in deep freezer (−20±5° C.) for at least 3 years, wherein the lyophilized drug substance consists of epoprostenol sodium salt and, related to the amount of the epoprostenol sodium salt, 3-7.5 mass % sodium hydroxide.

2. Drug substance as defined in claim 1, wherein the sodium hydroxide is in an amount of 4 mass %.

3. Drug substance as defined in claim 1, wherein the sodium hydroxide is in an amount of 5 mass %.

4. Drug substance as defined in claim 1, wherein the sodium hydroxide is in an amount of 6 mass %.

5. Process for the preparation of stable epoprostenol sodium drug substance of claim 1, which can be stored in deep freezer (−20±5° C.) for at least 3 years, comprising lyophilizing an aqueous solution of an epoprostenol sodium salt in the presence of such an amount of sodium hydroxide ensuring a pH>11 medium, that 3-7.5 mass % of excess sodium hydroxide, related to the amount of the epoprostenol sodium salt, is present in the lyophilisate.

6. Process for the preparation of stable epoprostenol sodium drug substance of claim 1, comprising cyclizing unprotected PGF2α with sodium iodide—sodium iodate mixture and eliminating hydrogen iodide, wherein
the cyclizing and eliminating are performed in the same solvent, and
lyophilizing an aqueous solution of the epoprostenol sodium salt in the presence of such an amount of sodium hydroxide ensuring a pH>11 medium that 3-7.5 mass % of excess sodium hydroxide, related to the amount of the epoprostenol sodium salt, is present in the lyophilisate.

7. Process as defined in claim 6, wherein a reaction mixture of PGF2α: sodium iodide: sodium-iodate=3:2:1 ratio is applied.

8. Process as defined in claim 6, wherein as solvent tetrahydrofuran is applied.

9. Process for the preparation of stable epoprostenol sodium drug substance of claim 5, wherein 4-6 mass % of excess sodium hydroxide is present in the lyophilisate.

* * * * *